US009808496B2

(12) United States Patent
Luc et al.

(10) Patent No.: US 9,808,496 B2
(45) Date of Patent: Nov. 7, 2017

(54) USE OF A MYRTLE EXTRACT AS AN ANTI-BIOFILM AGENT AGAINST *P. ACNES*

(71) Applicant: PIERRE FABRE DERMO-COSMETIQUE, Boulogne-Billancourt (FR)

(72) Inventors: Joelle Luc, Fenouillet (FR); Christel Fiorini-Puybaret, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 150 days.

(21) Appl. No.: 14/413,436

(22) PCT Filed: Jul. 8, 2013

(86) PCT No.: PCT/EP2013/064415
§ 371 (c)(1),
(2) Date: Jan. 8, 2015

(87) PCT Pub. No.: WO2014/009325
PCT Pub. Date: Jan. 16, 2014

(65) Prior Publication Data
US 2015/0190447 A1 Jul. 9, 2015

(30) Foreign Application Priority Data
Jul. 9, 2012 (FR) ..................... 12 56607

(51) Int. Cl.
A61K 36/00 (2006.01)
A61K 36/61 (2006.01)
A61K 8/97 (2017.01)
A61Q 19/00 (2006.01)
A61K 31/122 (2006.01)
A61K 31/19 (2006.01)
A61K 45/06 (2006.01)

(52) U.S. Cl.
CPC .............. *A61K 36/61* (2013.01); *A61K 8/97* (2013.01); *A61K 31/122* (2013.01); *A61K 31/19* (2013.01); *A61K 45/06* (2013.01); *A61Q 19/00* (2013.01)

(58) Field of Classification Search
None
See application file for complete search history.

(56) References Cited

FOREIGN PATENT DOCUMENTS

BR 2010004675 A2 * 7/2012
EP 1112079 7/2001
FR 2783425 A1 3/2000
WO WO 00/16791 A1 3/2000
WO WO 2012/053010 A2 4/2012

OTHER PUBLICATIONS

Fiorini-Puybaret et al, Pharmacological properties of Myrtacine∃ and its potential value in acne treatment. Planta medica, (Sep. 2011) vol. 77, No. 14, pp. 1582-1589. Electronic Publication Date: Mar. 30, 2011.*
Bayston et al., "Biofilm formation by Propionibacterium acnes on biomaterials in vitro and in vivo: impact on diagnosis and treatment," Journal of Biomedical Materials Research Part A, vol. 81, Published online Dec. 22, 2006, pp. 705-709.
Burkhart et al., "Expanding the microcomedone theory and acne therapeutics: Propionibacterium acnes biofilm produces biological glue that holds corneocytes together to form plug," Journal of the American Academy of Dermatology, vol. 57, Oct. 2007, pp. 722-724.
Burkhart et al., "Microbiology's principle of biofilms as a major factor in the pathogenesis of acne vulgaris," International Journal of Dermatology, vol. 42, 2003, pp. 925-927.
Campanac et al., "Interactions between Biocide Cationic Agents and Bacterial Biofilms," Antimicrobial Agents and Chemotherapy, vol. 46, No. 5, May 2002, pp. 1469-1474.
Coenye et al., "Biofilm formation by Propionibacterium acnes is associated with increased resistance to antimicrobial agents and increased production of putative virulence factors," Research in Microbiology, vol. 158, 2007 (Available online Feb. 21, 2007), pp. 386-392.
Coenye et al., "Biofilms in Skin Infections: Propionibacterium acnes and Acne Vulgaris," Infectious Disorders—Drug Targets, vol. 8, No. 3, 2008, pp. 156-159.
Fiorini-Puybaret et al., "Pharmacological Properties of Myrtacine and Its Potential Value in Acne Treatment," Planta Medica, vol. 77, No. 11, 2011 (Published online Mar. 30, 2011), pp. 1582-1589, XP002687346.
Holmberg et al., "Biofilm formation by Propionibacterium acnes is a characteristic of invasive isolates," Clinical Microbiology and Infection, vol. 15, No. 8, 2009 (Article published online Apr. 23, 2009), pp. 787-795.
International Search Report (Form PCT/ISA/210) for International Application No. PCT/EP2013/064415, dated Sep. 11, 2013, with an English translation.
Jahns et al., "An increased incidence of Propionibacterium acnes biofilms in acne vulgaris: a case-control study," British Journal of Dermatology, Feb. 22, 2012, pp. 1-9.
Ramage et al., "Formation of Propionibacterium acnes biofilms on orthopaedic biomaterials and their susceptibility to antimicrobials," Biomaterials, vol. 24, 2003, pp. 3221-3227.

* cited by examiner

*Primary Examiner* — Qiuwen Mi
(74) *Attorney, Agent, or Firm* — Birch, Stewart, Kolasch & Birch, LLP (57) ABSTRACT The invention relates to a dermatological composition containing a myrtle extract in a concentration that is higher than or equal to 0.01 wt. %, for the use thereof as an anti-biofilm agent against *Propionibacterium acnes*.

9 Claims, 5 Drawing Sheets

USE OF A MYRTLE EXTRACT AS AN ANTI-BIOFILM AGENT AGAINST P. ACNES

The present invention relates to the use in a dermatological composition of a myrtle extract as an anti-biofilm agent vis-à-vis *Propionibacterium acnes*.

Advantageously, the present invention relates to the use in a dermatological composition of a myrtle extract as an anti-adhesion agent against planktonic *Propionibacterium acnes* bacteria and/or as an agent for eradicating or destroying sessile *Propionibacterium acnes* bacteria organized into biofilm.

This myrtle extract as an anti-biofilm agent has also proven effective in decreasing resistance to antibiotics classically administered during the treatment of acne or folliculitis decalvans.

Acne is a common skin pathology which results from inflammation of pilosebaceous follicles, inflammation which is due, for the most part, to colonization of *Propionibacterium acnes* in the infundibulum.

Folliculitis decalvans is a chronic inflammatory pustulosis of the scalp which causes residual scarring alopecia. Folliculitis decalvans is an orphan disease whose physiopathology is poorly understood, but it is likely related to a predominantly neutrophilic inflammatory reaction to bacteria, likely *Propionibacterium acnes* bacteria.

The *P. acnes* bacterium metabolizes cutaneous triglycerides into irritating fatty acids via lipases that attack the follicle wall and the wall of the surrounding dermis, and also produces various enzymes and chemoattractants of immune system phagocytes which aggravate the inflammation.

Controlling this bacterial species is thus a priority when treating acne or folliculitis decalvans. Various topical antimicrobials are today widely used (benzoyl peroxide, clindamycin, erythromycin, triclosan).

A more or less lengthy systemic antibiotic therapy can be used in combination according to the severity of the ailment (tetracyclines, doxycycline, minocycline, erythromycin).

It has been noted, in recent years, that these treatments frequently fail due to the presence of a high proportion of *P. acnes* strains resistant to one or more antibiotics.

This increased resistance can arise when populations of planktonic bacteria (in suspension) organize into biofilm. Biofilms are communities of bacterial cells enclosed within an extracellular matrix excreted by microorganisms and composed of sugar polymers (extracellular polymeric substances, or EPS), called a glycocalyx. Biofilm is thus a polysaccharide shell which isolates the bacterium from the surrounding medium. The bacterium adapts its metabolism by slowing it. The biofilm thus allows the bacterium to:
- adhere to epithelial keratinocytes of the pilosebaceous follicle, which facilitates its modulation activities on keratinocyte differentiation and proliferation,
- develop into a colony in the pilosebaceous follicle, and
- become resistant to antibiotics used against acne, in particular cyclins and macrolides.

The biofilm lifestyle of bacteria is one of two lifestyles of unicellular organisms. This is the natural lifestyle of most microorganisms, in particular in hostile environments. In the second lifestyle bacteria float free in a liquid medium. Bacteria associated with the free-floating lifestyle are called planktonic bacteria. Bacteria associated with a biofilm are known as sessile bacteria.

Figure 1:
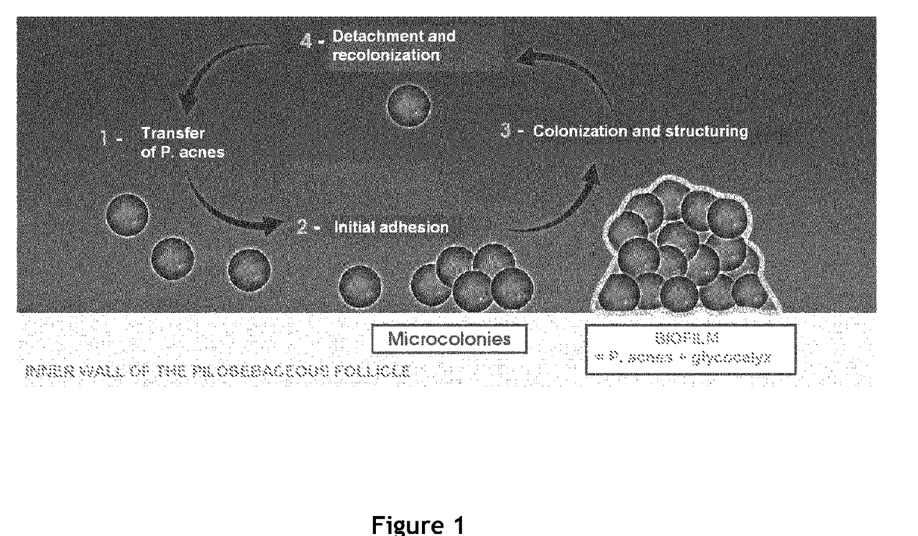
FIG. 1 depicts the formation of *P. acnes* biofilm in the pilosebaceous follicle proceeds in four stages.

As shown in FIG. 1, the formation of *P. acnes* biofilm in the pilosebaceous follicle proceeds in four stages:
1) transfer of planktonic *P. acnes* towards the inner wall of the pilosebaceous follicle
2) initial adhesion of *P. acnes* on the wall
3) colonization and structuring of sessile *P. acnes*
4) detachment of *P. acnes* and recolonization.

Sessile bacteria (associated with biofilm) are phenotypically and physiologically different from planktonic (free) bacteria.

This organization into biofilm has been put forth to explain the therapeutic failures of acne treatments (Burkart C. N., Burkart C. G., 2003. Microbiology's principle of biofilms as a major factor in the pathogenesis of acne vulgaris. Int. J. Dermatol. 42. 925-927).

Recent studies have confirmed the ability of *P. acnes* to form biofilms, both:
- in vitro (Bayston R., Ashraf W., Barker-Davis R., Tucker E., Clement R., Clayton J., Freeman B. J., Nuradeen B. 2007. Biofilm formation by *Propionibacterium acnes* on biomaterials in vitro and in vivo: impact on diagnosis and treatment. J. Biomed. Mast. Res. A81, 705-709) (Coneye T., Peeters E., Nelis H. J. 2007a. Biofilm formation by *Propionibacterium acnes* is associated with increased resistance against antimicrobial agents and increased production of putative virulence factors. Res. Microbiol. 158. 386-392) (Holmberg A., Lood R., Mörgelin M., Söderquist B., Holst E., Collin M., Christensson B., Rasmussen M. 2009. Biofilm formation by *Propionibacterium acnes* is a characteristic of invasive isolates. Clin. Microbiol. Infect. 15, 787-795)
- in vivo on medical devices (Coneye T., Honraet K., Rossel B., Nelys H. J., Biofilm in skin infection: *Propionibacterium acnes* and acne vulgaris. Infect Disord Drug Target 2008. 14. 649-659) (Ramage G., Tunney M. M., Patrick S., Gorman S. P. and Nixon J. R. 2003. Formation of *Propionibacterium acnes* biofilms on orthopedic biomaterials and their susceptibility to antimicrobials. Biomaterials; 24: 3221-3227) (Craig G., Burkhart M. D., Craig N. 2007. Expanding the microcomedone theory and acne therapeutics: *Propionibacterium acnes* biofilm produces biological glue that holds corneocytes together to form plug. J Am Acad Dermatol. October).

Even recent technologies do not make it possible to visualize biofilm in follicles in situ, but a recent study was able to detect the presence of *P. acnes* macrocolonies/biofilm in pilosebaceous follicles from skin biopsies (Jahns A. C., Lundskog B., Ganceviciene R., Palmer R. H., Golovleva I., Zouboulis D. C., McDowell A., Patrick S., Alexeyev O. A. 2012. An increased incidence of *Propionibacterium acnes* biofilms in acne vulgaris: a case-control study. Br J Dermatol. February 22).

The concept of *P. acnes* biofilm, generally accepted today, opens the way to new therapeutic targets, such as: inhibiting the formation of biofilm, or inhibiting the spread of or the chemical or mechanical eradication of biofilm already formed.

These approaches are alternatives to the biocidal activity classically used to prevent microorganisms from taking hold. These two types of activity, biocidal and anti-biofilm, bring into play different properties, one not suggesting the other.

The present invention aims to show the activity of myrtle extract, on the one hand to inhibit the formation of *P. acnes* biofilm, and on the other hand to inhibit the spread or to eradicate (or destroy) biofilm already formed.

The present invention relates to work undertaken on the species *Myrtus communis*.

Preferably, the extract is prepared from the leaves of *Myrtus communis*.

Preferably, the extract is a non-polar fraction from the aerial parts of myrtle.

The extract of the present invention can be obtained via extraction using a solvent or a mixture of solvents selected from:
alcohols such as ethanol, methanol, isopropanol
ketones including acetone and methylethylacetone
hexane
methylene chloride
isopropyl ether
ethyl acetate;
or by supercritical $CO_2$.

The extract can also be stabilized by adding an antioxidant, such as butylhydroxytoluene or α-tocopherol, for example, in quantities between 0.05 and 1 g/100 g of dry extract.

The extract of the present invention has the feature of being rich in myrtucommulones and ursolic acid. Myrtucommulones A, B', D, B, isoS (isosemimyrtucommulone) and S (semimyrtucommulone) are the principal myrtucommulones present.

Advantageously, the total myrtucommulone content in the extract is between 3 and 10% by weight.

The ursolic acid content is between 10 and 30%, preferably ≥15% by weight.

These molecules have the activity claimed in the context of the present invention.

In a particular embodiment of the invention, the myrtle extract will preferably be as described in patent EP 1 112 079. This document describes the antibacterial properties of *Myrtus communis* extract and applications thereof in cosmetic or dermatological compositions.

An altogether remarkable aspect of the present invention is that the anti-biofilm activity of the composition of the invention is observed even at very low concentrations of myrtle extract, i.e., as low as 0.01% by weight in relation to the total weight of the composition.

The quantity of extract in the composition is between 0.01% and 1%, and is preferably between 0.03% and 1%.

Advantageously, the quantity of extract is less than or equal to 0.1%.

More particularly, the quantity of extract is greater than or equal to 0.01% and less than or equal to 0.1%. Even more preferably, the quantity of extract is greater than or equal to 0.03% and less than or equal to 0.1%.

By "anti-biofilm agent vis-à-vis *Propionibacterium acnes*" is meant, in the context of the present invention, an agent which:
inhibits the adhesion of *Propionibacterium acnes* biofilm (to avoid the formation of *Propionibacterium acnes* biofilm), and/or
eradicates *Propionibacterium acnes* biofilm already formed (destruction, detachment).

In order to demonstrate the activity of the anti-biofilm agent, a dynamic model of biofilm formation on an inert support, already used in other areas of research (Campanac C., Pineau L., Payard M., Baziard-Mouysset G., Roques C. 2002. Interaction between biocide cationic agents and bacterial biofilms. Antimicrob. Ag. Chemother. May 46 (5) 1469-1474), was applied specifically to *P. acnes*. Thus, the two aspects mentioned were explored:
Influence of the extract on the genesis of *P. acnes* biofilm: this activity brings into play structures involved in the adhesion of cells on a surface and in the structuring of biofilm,
Eradication of biofilm already formed, bringing into play other properties (cleaning, etc.).

The myrtle extract of the invention helps fight *P. acnes* by limiting its organization into biofilm. This action of preventing planktonic *P. acnes* bacteria from adhering and of breaking down *P. acnes* biofilm already formed, promotes the disappearance of acne lesions from acne skin and/or from oily, acne-prone skin.

The Applicant pursued its research into the use of myrtle extract as an anti-biofilm agent, and discovered in a surprising and unexpected manner that myrtle extract decreases the resistance of *P. acnes* strains—preferentially *P. acnes* strains organized into biofilm—to administered antibiotics acting on *P. acnes*, preferably in topical form.

The present invention thus relates to a dermatological composition containing myrtle extract at a concentration greater than or equal to 0.01% by weight, for use as an anti-biofilm agent vis-à-vis *Propionibacterium acnes*.

Advantageously, the present invention relates to a dermatological composition containing myrtle extract at a concentration greater than or equal to 0.01% by weight, for use as an anti-adhesion agent against planktonic *Propionibacterium acnes* bacteria and/or as an agent for eradicating or destroying sessile *Propionibacterium acnes* bacteria organized into biofilm.

In particular, the present invention relates to a dermatological composition containing myrtle extract at a concentration greater than or equal to 0.01% by weight, for use as an anti-adhesion agent against planktonic bacteria in order to promote the free-floating thereof.

More particularly, the present invention relates to a dermatological composition containing myrtle extract at a concentration greater than or equal to 0.01% by weight, for use as an anti-biofilm agent to prevent adhesion of planktonic bacteria.

More particularly, the present invention relates to a dermatological composition containing myrtle extract at a concentration greater than or equal to 0.01% by weight, for preventive use against reorganization of planktonic bacteria into biofilm once a biofilm is destroyed.

Another aspect of the present invention relates to a composition containing myrtle extract at a concentration of 0.01% to 1% by weight.

According to another aspect of the present invention, the quantity of extract is greater than or equal to 0.01% and less than or equal to 0.1% by weight.

According to another aspect of the present invention, the myrtle extract is a non-polar fraction consisting of myrtucommulones and ursolic acid.

The topical use of the composition of the present invention is intended to decrease resistance to an antibiotic administered preferably in topical form and acting on *P. acnes*.

According to another aspect of the present invention, the composition is used in the treatment of acne or folliculitis decalvans.

According to another aspect, the present invention relates to a combination product consisting of a dermatological composition containing myrtle extract at a concentration of 0.01% to 1% by weight and a dermatological composition containing at least one antibiotic, in particular, a topical antibiotic active against *P. acnes*, for simultaneous, separate or sequential use in the treatment of acne or folliculitis decalvans.

The dermatological composition of the combination product of the invention contains a quantity of myrtle extract greater than or equal to 0.01% and less than or equal to 0.1% by weight.

According to another aspect of the invention, the myrtle extract is at a concentration of 0.1% by weight.

The aforesaid antibiotics classically used are erythromycin, doxycycline and clindamycin.

The anti-biofilm agent of the invention improves the therapeutic efficacy of the antibiotic.

The antibiotics mentioned above combined with myrtle extract have minimum inhibitory concentrations (MICs) lower than those of the antibiotics alone.

The MIC is the lowest concentration of a product that will inhibit the growth of bacteria.

In the context of acne treatment, there is a real advantage in combining antibiotic therapy with the application of a composition containing myrtle extract as an anti-biofilm agent. Indeed, this decreases the resistance of certain *P. acnes* strains to erythromycin or to clindamycin.

Formulation/Preparation

The composition of the present invention can be provided in any form suitable for topical application: cream, gel, stick, serum.

The invention can be better understood with the aid of the following pharmacological examples and evaluations:

EXAMPLES

1—Preparation of Extract 1.1—Example 1

1 kg of crushed myrtle leaves is extracted with 10 volumes of isopropyl acetate with stirring at reflux. Extract at reflux for 1 hour with stirring. After the marc is filtered and rinsed, the extraction juice is decolorized by adding activated carbon. After being filtered, the decolorized filtrate is concentrated to 2 liters and then dried on water until the isopropyl acetate is removed. The aqueous phase obtained is then freeze-dried.

1 kg of myrtle leaves yields about 25 g of dry myrtle extract.

The latter contains 7% of myrtucommulones and 25% of ursolic acid.

1.2—Example 2

1 kg of crushed myrtle leaves is extracted with 5 volumes of isopropyl acetate with stirring at reflux for 1 hour. After the marc is filtered and rinsed, the extraction juice is decolorized by adding activated carbon. After being filtered, the decolorized filtrate is concentrated to 2 liters and then dried on ethanol until the isopropyl acetate is removed. The aqueous phase obtained is then deodorized by heat treatment and then freeze-dried.

1 kg of myrtle leaves yields approximately 25 g of dry myrtle extract.

The latter contains 7% of myrtucommulones and 25% of ursolic acid.

2—Formulations 2.1—Example 3: Formula for Cleansing Gel

Zinc coceth sulfate (Zetesol Zn®, Zchimmer&Schwarz), 5 to 20%
DECYL GLUCOSIDE
LAURYL BETAINE
Polysorbate 20, 0.5 to 4%
PEG-5 ETHYLHEXANOATE, 1 to 3%
Ceteareth-60 myristyl glycol, 0.5 to 3%
ZINC SALICYLATE, 0.1 to 0.5%
SERENOA REPENS EXT., 0.1 to 0.3%
LIPOPHILIC DRY MYRTLE EXT., 0.01 to 0.1%
SODIUM BENZOATE/CITRIC ACID/SODIUM HYDROXIDE qs 2.2—Example 4: Cream Myrtle extract, 0.03 to 0.1%
AHA BHA, 1 to 8%
Xanthan gum, 0.1%
Dimethicone, 1%
Cetostearyl isononanoate, 12%
Glyceryl stearate, 2%
Cetearyl alcohol & Ceteareth-33, 6%
Polymethyl methacrylate, 2%
Water qs 100%
Evaluation Obtaining *P. acnes* biofilm in a continuous flow The apparatus used to form the biofilm is shown in FIG. 2.

The two pumps used serve to, respectively:
supply the loop with substrate (pump no. 1),
stir of the contents of the system (pump no. 2).

Figure 2:
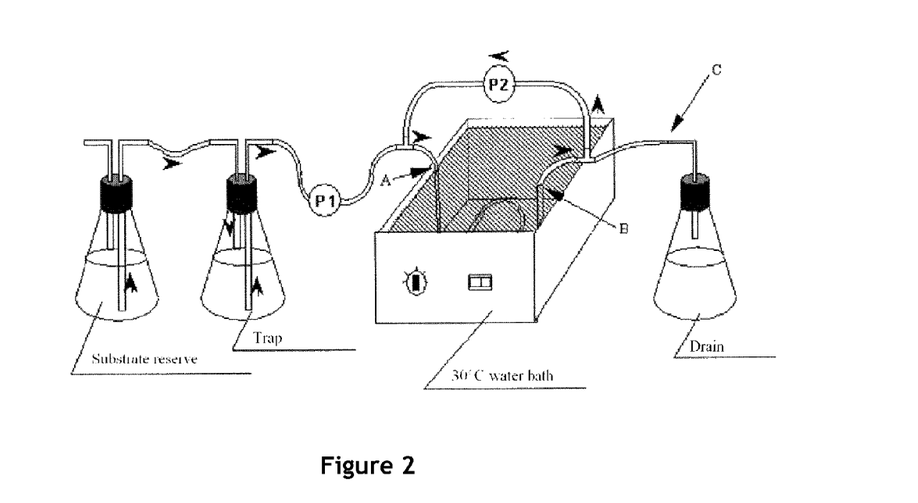
FIG. 2 depicts the apparatus used to form the biofilm.

The whole of the experimental apparatus described in FIG. 2 is placed under a laminar flow hood.

The system is supplied with culture medium. The medium is then inoculated by injecting, at point B, a quantity of bacterial suspension of *P. acnes* CIP 53117 in order to obtain a final concentration in microorganisms of about $10^7$ CFU/ml.

The microorganisms of the inoculum are distributed throughout the loop, i.e., a homogenization phase followed by a supply of substrate via pump no. 1.

After forming for 48 hours, a *P. acnes* CIP 53117 biofilm is obtained.

In the experimental apparatus shown in FIG. 2, the references in the drawing have the following meanings:

P1: Pump for supplying substrate
P2: Pump for stirring the system
A-B, lower section: Area for sampling sections of tube
B: Area for inoculating the loop.
A-B, upper section: Section of tube containing pump P2.
EVALUATION of the myrtle extract's inhibition of adhesion on the formation of P. acnes biofilm.

In order to evaluate the adhesion inhibition effect of the dry myrtle extract prepared according to example 2 on the formation of P. acnes CIP 53117 biofilm, two apparatus were prepared as described in the preceding paragraph. The first serves as a control. The second is supplied culture medium supplemented with dry myrtle extract at a final concentration of 0.1% (non-lethal concentration). The test is carried out twice.

Adhered and planktonic bacteria were counted at 5 h, 24 h and 48 h on the "treated" support versus an untreated control according to the following protocol. The tube sample is cut longitudinally into four identical sections and the inner surface of each of these portions is scraped using a sterile scalpel blade into 10 ml of diluent.

The tube sections and the liquid are then transferred to a test tube and shaken for about 1 minute.

The bacteria are then streaked on agar culture medium and counted.

At the same time, a sample of effluent is recovered for counting planktonic bacteria, according to the same protocol.

The plates are incubated at 37±2° C. under anaerobic conditions.

The CFUs are counted after 96 hours of incubation.

The results are expressed in CFU/cm$^2$ for adhered bacteria and CFU/ml of effluent for planktonic bacteria.

Results

The results obtained are presented in table 1.

The estimate of cultivable adhered population is expressed in log CFU/cm$^2$ of tube and that of cultivable planktonic population in log CFU/ml.

TABLE 1

Results of inhibition of adhesion of P. acnes by 0.1% (w/v) dry myrtle extract. Results expressed in log (CFU/cm$^2$ or ml).

| | | Control | | Dry myrtle extract, 0.1% (w/v) | |
|---|---|---|---|---|---|
| Formation time | Test | Adhered Log (CFU/cm$^2$) | Planktonic Log (CFU/ml) | Adhered Log (CFU/cm$^2$) | Planktonic Log (CFU/ml) |
| 5 hours | Test 1 | 4.28 | 5.11 | 3.23 | 4.04 |
| | Test 2 | 4.57 | 4.97 | 3.20 | 4.51 |
| | Mean | 4.42 | 5.04 | 3.22 | 4.27 |
| 24 hours | Test 1 | 4.08 | 3.67 | 0.70 | 3.93 |
| | Test 2 | 4.77 | 3.18 | 2.77 | 3.32 |
| | Mean | 4.43 | 3.42 | 1.73 | 3.63 |
| 48 hours | Test 1 | 4.18 | 2.38 | 2.04 | 1 |
| | Test 2 | 3.46 | 3.23 | 0.48 | 1.08 |
| | Mean | 3.82 | 2.81 | 1.26 | 1.04 |

Figure 3:
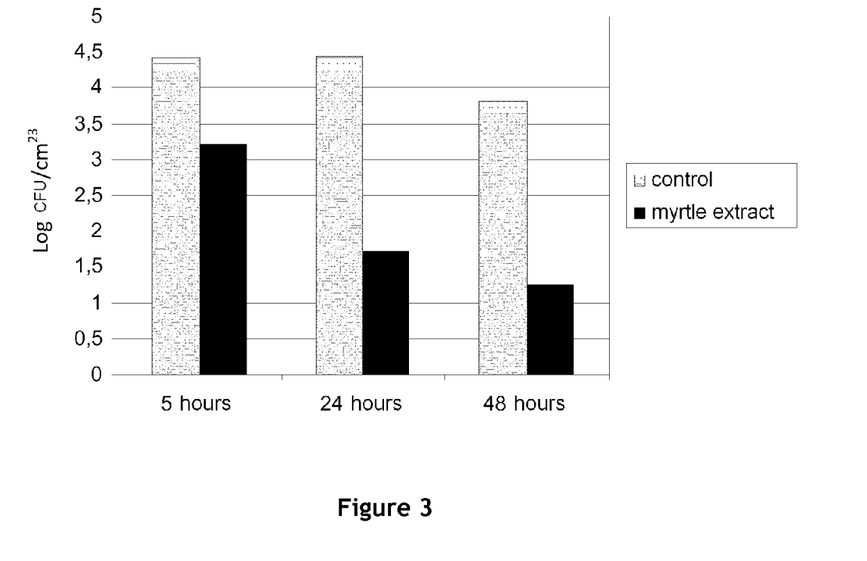
FIG. 3 shows the means of the results obtained for adhered populations, expressed in log $CFU/cm^2$.

The means of the results obtained for adhered populations, expressed in log CFU/cm$^2$, are shown in FIG. 3 below.

Inhibition of adhesion of P. acnes is observed 5 hours after inoculation for the apparatus with dry myrtle extract. This inhibition is on the order of 1.2 log. The estimate of the planktonic population is of the same order for both apparatus (treated and control). After 24 hours of formation, the phenomenon persists with inhibition on the order of 2.7 log.

After 48 hours, this inhibition stayed constant, on the order of 2.6 log. During this period of time, a significant decrease in the cultivable planktonic population is observed for both apparatus (treated and control).

These results show inhibition of adhesion, under the test conditions, induced by the 0.1% (w/v) dry myrtle extract.

Evaluation of Detachment Activity

The detachment activity of the dry myrtle extract prepared according to example 2 was evaluated on P. acnes CIP 53117 biofilm obtained after 48 hours of formation as described before.

The test conditions (cf. FIG. 4) are as follows:
Detachment activity of 0.1% (w/v) dry myrtle extract versus sterile distilled water,
Contact time: 1.5 and 10 minutes of contact,
Room temperature.

After each defined contact time, various samples are taken:
a sample of tube (2 cm) for counting residual bacteria,
a sample of circulating solution for counting suspended bacteria.

Figure 4:
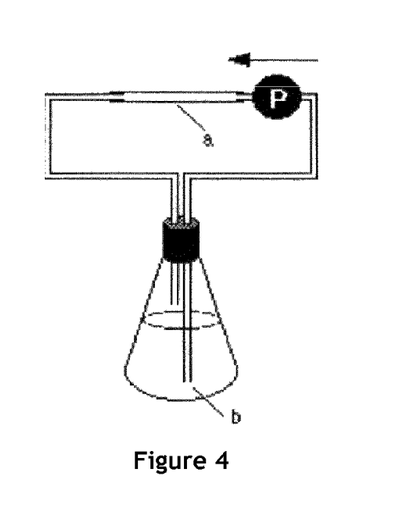
FIG. 4 shows the experimental apparatus used to evaluate the detachment activity of the dry myrtle extract prepared according to example 2 on *P. acnes* CIP 53117 biofilm obtained after 48 hours of formation.

In the experimental apparatus shown in FIG. 4, the references have the following meanings:
a=sample of tube for counting residual bacteria
b=circulating solution
P=pump.

The test is carried out in duplicate for the dry myrtle extract and once for the sterile distilled water.

The number of adhered microorganisms was counted before the various treatments (control) were begun.

Results

The results obtained are presented in table 2. The estimate of the cultivable adhered population is expressed in log CFU/cm$^2$ of tube and that of planktonic cultivable population in log CFU/200 ml (volume of circulating solution).

TABLE 2

Results of detachment activity of 0.1% (w/v) dry myrtle extract solution versus sterile distilled water (SDW) on P. acnes biofilm (after 48 h of formation). Results expressed in log (CFU/cm$^2$ or ml).

| Contact time | Test | Sterile distilled water Adhered Log (CFU/cm$^2$) | Dry myrtle extract, 0.1% (w/v) Adhered Log (CFU/cm$^2$) |
|---|---|---|---|
| T0 | Test 1 | 4.46 | 4.46 |
| | Test 2 | 4.23 | 4.23 |
| | Mean | 4.35 | 4.35 |
| 1 minute | Test 1 | 3.28 | 1.00 |
| | Test 2 | — | 1.72 |
| | Mean | 3.28 | 1.36 |
| 5 minutes | Test 1 | 4.00 | 0.90 |
| | Test 2 | — | 0.48 |
| | Mean | 4.00 | 0.69 |
| 10 minutes | Test 1 | 3.30 | 0.48 |
| | Test 2 | | 0.90 |
| | Mean | 3.30 | 0.69 |

The control series prepared with sterile distilled water validated the test since no notable reduction of cultivable adhered population is observed (<1 log of reduction=removal of the first surface layers of the biofilm).

Figure 5:
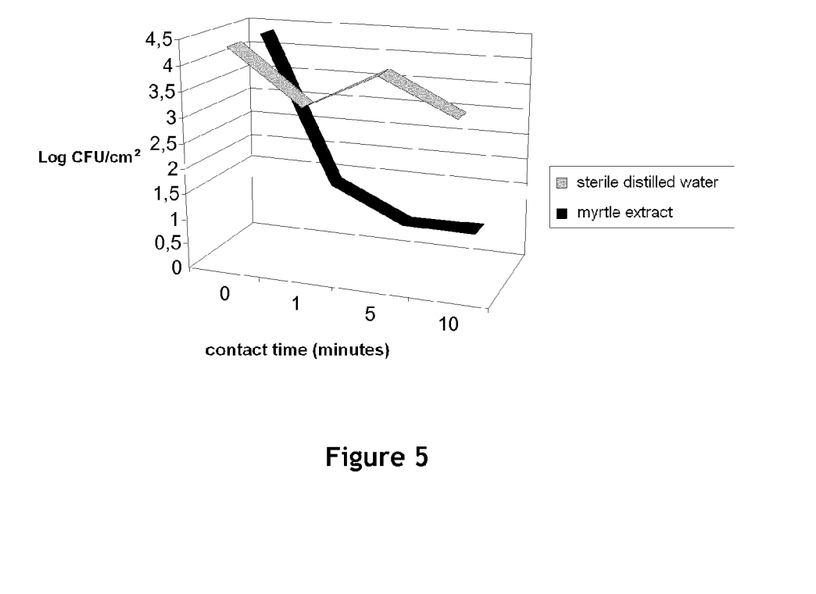
FIG. 5 shows the detachment activity of 0.1% (w/v) dry myrtle extract solution versus sterile distilled water on *P. acnes* biofilm (after 48 h of formation) expressed in log ($CFU/cm^2$).

The detachment activity of 0.1% (w/v) dry myrtle extract solution versus sterile distilled water on P. acnes biofilm (after 48 h of formation) expressed in log (CFU/cm$^2$) is shown in FIG. 5.

In the presence of 0.1% (w/v) dry myrtle extract, a significant decrease in the adhered population is observed. The decrease is on the order of 3 log after 1 minute of contact.

Lengthening the circulation time of the solution from 1 to 5 minutes provides an additional increase in terms of detachment of about 0.7 log.

Evaluation of the Activity of the Combination Erythromycin/Myrtle Extract on *P. acnes* Biofilm Myrtle extract is prepared according to example 2.

Identification of Strains

Four *Propionibacterium acnes* strains were selected:

Two Erythromycin-Resistant Strains (ERY R)

*Propionibacterium acnes* CIP 110371 clinical isolate R4

Two Erythromycin-Sensitive Strains (ERY S)

*Propionibacterium acnes* CIP 53117T clinical isolate B872

Protocol

A titrated suspension of *P. acnes* (about $10^6$ CFU/ml), in minimal broth allowing no bacterial growth, was deposited in the wells of a 24-well microplate.

The microplates are placed under anaerobic conditions at 37±2° C. for 48 h, the time established for biofilm to form.

After 48 h, the supernatant of each well is discarded and then the wells are rinsed. Erythromycin and myrtle extract at various concentrations are added for a contact time of 24 h on the adhered cells (72 hours of adhesion in total).

The erythromycin concentration selected is 1000 µg/ml. At this concentration it was verified, on isolated bacteria, that this antibiotic had bactericidal activity (between 4 and 5 log of reduction in 24 hours) vis-à-vis the two erythromycin-sensitive strains (ERY S) and did not have bactericidal activity vis-à-vis the two erythromycin-resistant strains (ERY R).

After 72 h of adhesion:

planktonic cells are counted adhered (sessile) cells are counted after rinsing the well and then scraping in tryptone salt Controls were prepared in parallel (adhered+planktonic cells)

72 h biofilm control (with the medium changed at 48 h)

myrtle control at various concentrations (added after 48 h/24 h of contact)

1000 µg/ml erythromycin control (added at 48 h/24 h of contact)

myrtle extract control at the concentrations tested

For all the wells in contact with erythromycin, 1 ml of each dilution is filtered on a membrane (Microfil®, Millipore) and then the filter is rinsed three times with 50 ml of sterile distilled water. The membranes are deposited on Columbia agar+5% sheep blood. The plates are incubated at 37±2° C. under anaerobic conditions. After 72 h to 96 h of incubation, the colony forming units (CFUs) are counted.

For all the biofilm controls and the myrtle extract alone, 100 µl of each dilution is inoculated by streaking on Columbia agar+5% sheep blood. The plates are incubated at 37±2° C. under anaerobic conditions. After 72 h to 96 h of incubation, the CFUs are counted.

Results

This test consisted in evaluating the activity of erythromycin (1000 µg/ml) combined with myrtle extract, at concentrations of 0.03%, 0.001% and 0.0001%.

The results are expressed in log of the population counted.

TABLE 3

Collection strains/Limit of detection at 1.3 log

| | | Log (number of CFU/well) | | | |
|---|---|---|---|---|---|
| | | *P. acnes* CIP 53117T (eryS) | | *P. acnes* CIP 110371 (eryR) | |
| | Conditions | Adhered cells | Planktonic cells | Adhered cells | Planktonic cells |
| T | Control | 5.1 | 5.5 | 5.3 | 5.0 |
| 72 h | 1000 Ery control | 4.3 | 1.3 | 4.1 | 4.2 |
| | 0.03% Myr control | 1.3 | 1.3 | 1.3 | 1.3 |
| | 0.001% Myr control | 3.5 | 3.6 | 3.8 | 4.1 |
| | 0.0001% Myr control | 5.0 | 5.2 | 4.6 | 5.2 |
| | 1000 Ery + 0.03% Myr | 1.3 | 1.3 | 1.3 | 1.3 |
| | 1000 Ery + 0.001% Myr | 2.4 | 1.3 | 2.1 | 2.9 |
| | 1000 Ery + 0.0001% Myr | 3.0 | 1.3 | 2.4 | 2.8 |

Results for ERY S—Collection Strains

Figure 6:
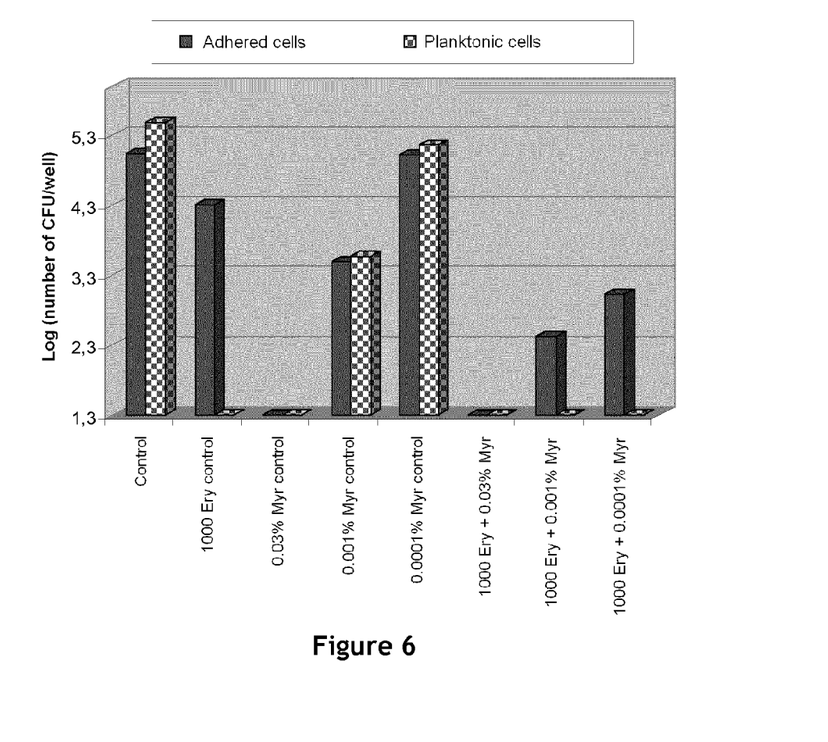
FIG. 6 shows the activity of erythromycin (1000 µg/ml) combined with myrtle extract, at concentrations of 0.03%, 0.001% and 0.0001%.

The activity of erythromycin (1000 µg/ml) combined with myrtle extract, at concentrations of 0.03%, 0.001% and 0.0001%, is shown in FIG. 6.

Results for ERY R—Collection Strains

Figure 7:
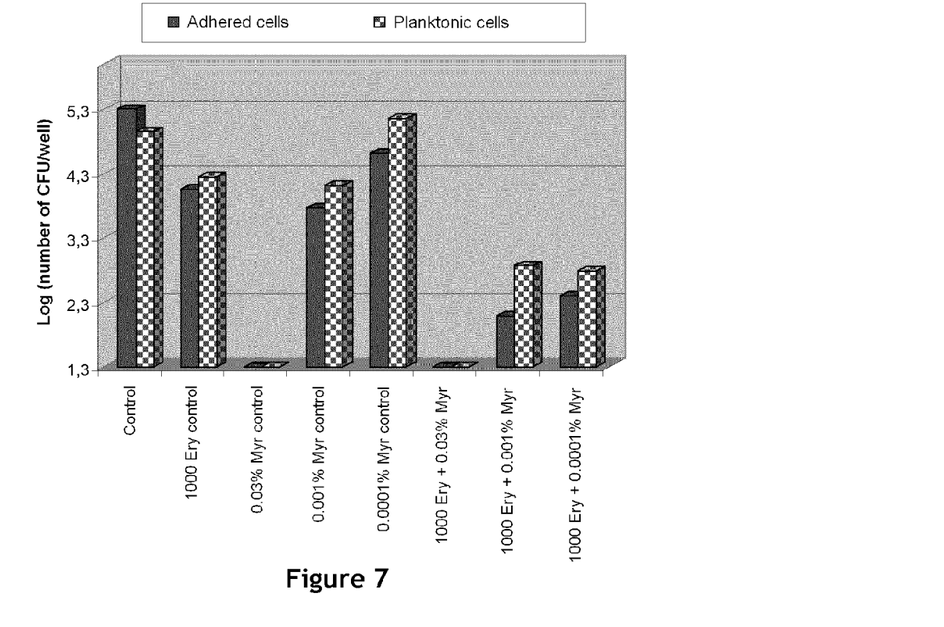
FIG. 7 shows the activity of erythromycin (1000 µg/ml) combined with myrtle extract, at concentrations of 0.03%, 0.001% and 0.0001%.

The activity of erythromycin (1000 µg/ml) combined with myrtle extract, at concentrations of 0.03%, 0.001% and 0.0001%, is shown in FIG. 7.

TABLE 4

Isolates

| | | Log (number of CFU/well) | | | |
|---|---|---|---|---|---|
| | | *P. acnes* B872 (eryS) | | *P. acnes* R4 (eryR) | |
| | Conditions | Adhered cells | Planktonic cells | Adhered cells | Planktonic cells |
| T | Control | 4.4 | 4.0 | 4.5 | 3.7 |
| 72 h | 1000 Ery control | 4.0 | 1.3 | 3.5 | 3.5 |
| | 0.03% Myr control | 1.3 | 1.3 | 1.3 | 1.3 |
| | 0.001% Myr control | 3.6 | 3.4 | 3.7 | 3.5 |
| | 0.0001% Myr control | 4.4 | 4.2 | 4.6 | 4.4 |
| | 1000 Ery + 0.03% Myr | 1.4 | 1.3 | 1.4 | 1.3 |
| | 1000 Ery + 0.001% Myr | 2.3 | 1.3 | 1.8 | 2.0 |
| | 1000 Ery + 0.0001% Myr | 2.4 | 1.3 | 2.5 | 3.2 |

Results for ERY S—Isolates

Figure 8:
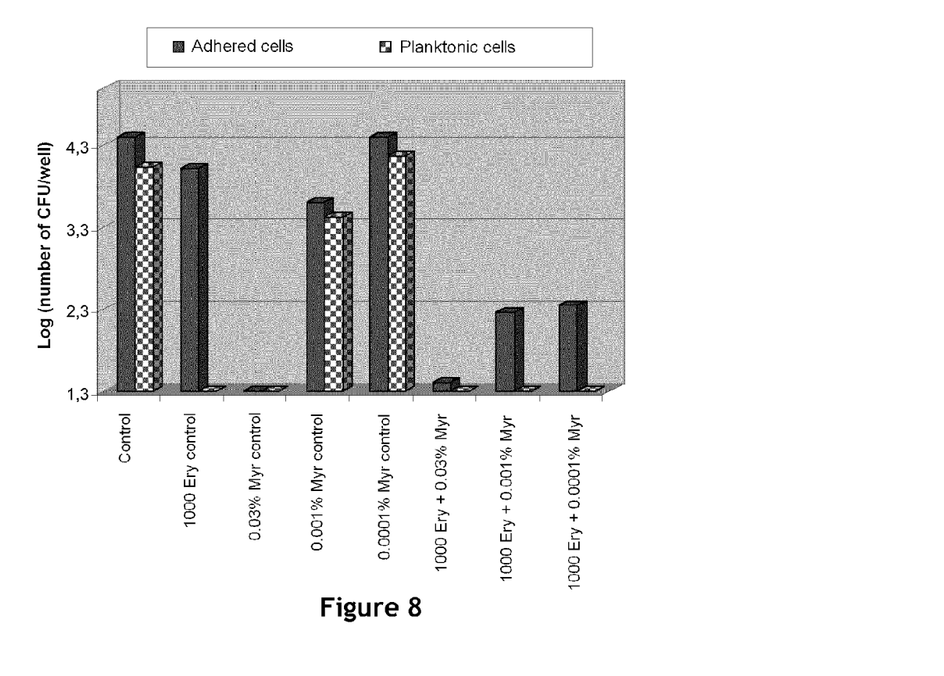
FIG. 8 shows the activity of erythromycin (1000 µg/ml) combined with myrtle extract, at concentrations of 0.03%, 0.001% and 0.0001%.

The activity of erythromycin (1000 µg/ml) combined with myrtle extract, at concentrations of 0.03%, 0.001% and 0.0001%, is shown in FIG. 8.

Results for ERY R—Isolates

Figure 9:
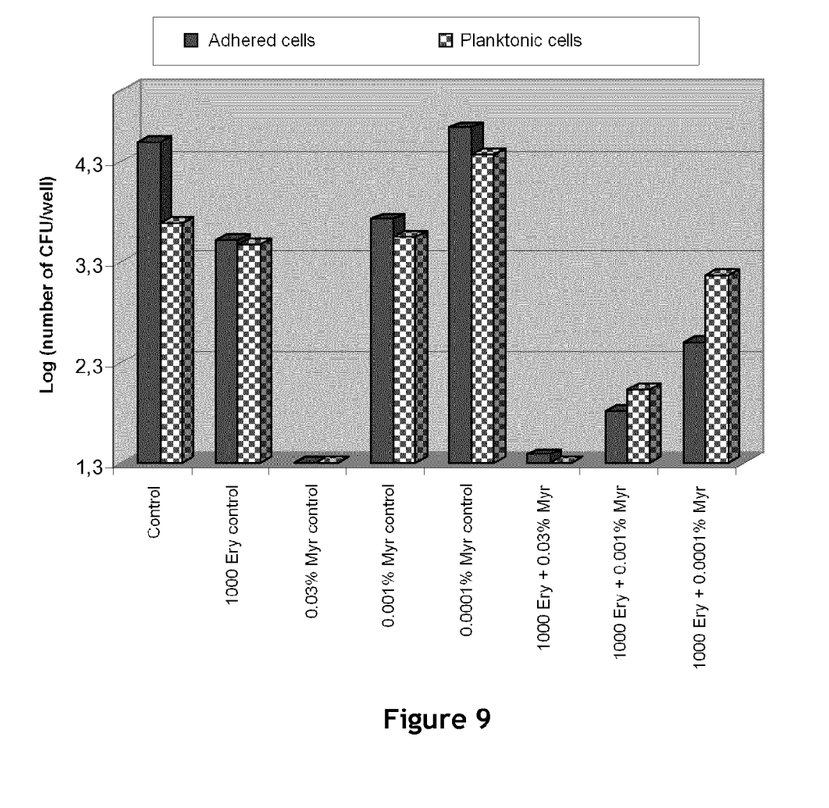
FIG. 9 shows the activity of erythromycin (1000 µg/ml) combined with myrtle extract, at concentrations of 0.03%, 0.001% and 0.0001%.

The activity of erythromycin (1000 µg/ml) combined with myrtle extract, at concentrations of 0.03%, 0.001% and 0.0001%, is shown in FIG. 9.

GENERAL CONCLUSION

Extract Alone:

Myrtle extract alone, at a concentration of 0.03%, is observed to have high activity vis-à-vis both eryS strains and eryR strains.

The results obtained also illustrate that myrtle extract alone has significant activity—certainly on planktonic bacteria—but also on adhered *P. acnes* bacteria (dose-dependent effect).

The less active myrtle extract concentrations (0.001% and 0.001%) were chosen to demonstrate the effects of the combination myrtle extract/erythromycin-type antibiotic treatment.

Erythromycin Alone:

The results confirm that the organization of *P. acnes* bacteria into biofilm (eryS and eryR) decreases their sensitivity to erythromycin.

It was verified in addition that eryR planktonic strains exhibit resistance to erythromycin.

Lastly, the bactericidal activity of erythromycin is high on the eryS strains.

Combination of Myrtle Extract and Erythromycin:

Destruction of the biofilm (decreased number of *P. acnes* bacteria organized into biofilm) and elimination of a portion of the planktonic population (bacteria detached from the biofilm) are observed for the three pairs evaluated. An additional decrease of at least 1 log in the adhered population is observed for the lowest concentrations of myrtle extract (0.001% and 0.0001%) combined with erythromycin, in comparison with erythromycin alone or extract alone. For the higher concentration of myrtle extract (0.03%), the synergistic effect is masked by the high activity of the extract.

Thus, a potentiation of action was indeed observed by combining myrtle extract with a reference antibiotic. Indeed, myrtle extract decreases the resistance of *P. acnes* strains in biofilm form to the reference molecule in antibiotic therapy. Myrtle extract optimizes the action of erythromycin vis-à-vis *P. acnes* bacteria.

The invention claimed is:

1. A method for treating acne or folliculitis decalvans comprising: topically administering to a person in need thereof of an effective amount of a first dermatological composition containing myrtle extract at a concentration of 0.01% to 1% by weight, and further comprising the simultaneous, separate or sequential administration of a second dermatological composition containing at least one antibiotic.

2. The method according to claim 1, wherein the first dermatological composition contains a quantity of myrtle extract greater than or equal to 0.01% and less than or equal to 0.1% by weight.

3. The method according to claim 1, wherein the myrtle extract is a non-polar fraction comprising myrtucommulones and ursolic acid.

4. The method according to claim 3, wherein said myrtucommulones comprise mainly myrtucommulones A, B', D, B, isosemimyrtucommulone and semimyrtucommulone.

5. The method according to claim 3, wherein the total myrtucommulone content is between 3% and 10% by weight, in relation to the total weight of the myrtle extract.

6. The method according to claim 3, wherein the ursolic acid content is between 10% and 30% by weight, in relation to the total weight of the myrtle extract.

7. The method according to claim 6, wherein the ursolic acid content is less than 15% by weight, in relation to the total weight of the myrtle extract.

8. The method according to claim 1, wherein the second dermatological composition is administered in a topical form.

9. The method according to claim 1, wherein the antibiotic is erythromycin.

* * * * *